United States Patent [19]

Vince

[11] Patent Number: 4,877,659
[45] Date of Patent: Oct. 31, 1989

[54] MULTIWELL ASSAY/CULTURE STRIP

[75] Inventor: Paul W. Vince, San Rafael, Calif.

[73] Assignee: Inti Corporation, San Rafael, Calif.

[21] Appl. No.: 227,508

[22] Filed: Aug. 2, 1988

[51] Int. Cl.$^4$ ............................................. C12M 1/32
[52] U.S. Cl. .................................. 428/34.1; 206/558; 435/293; 435/300; 435/301; 428/99
[58] Field of Search ................. 435/293, 300, 301; 206/558; 428/99, 34.1, 35.7

[56] References Cited

U.S. PATENT DOCUMENTS

| | | | |
|---|---|---|---|
| 3,649,464 | 3/1972 | Freeman | 206/558 |
| 3,713,985 | 1/1973 | Astle | 435/301 |
| 4,072,578 | 2/1978 | Cady et al. | 435/300 |
| 4,090,920 | 5/1978 | Studer, Jr. | 435/300 |
| 4,599,314 | 7/1986 | Shami | 435/300 |

Primary Examiner—Ellis P. Robinson
Assistant Examiner—James J. Seidleck
Attorney, Agent, or Firm—Larry D. Johnson

[57] ABSTRACT

A multiwell assay/culture strip provides an improved structure for a strip of wells as used for culturing cells and diagnostic testing, and comprises a strip or segment of generally identical well portions (typically eight or twelve wells) in linear arrangement adjacent one another and supported by a common base, and terminating in a first end and a second end. Each end bears a linking member extending perpendicularly from the end, and carries a receiver member conditioned to accept and frictionally engage an appropriate linking member of a separate strip. The linking members further provide offset basal surfaces to enhance stability of the strip.

4 Claims, 3 Drawing Sheets

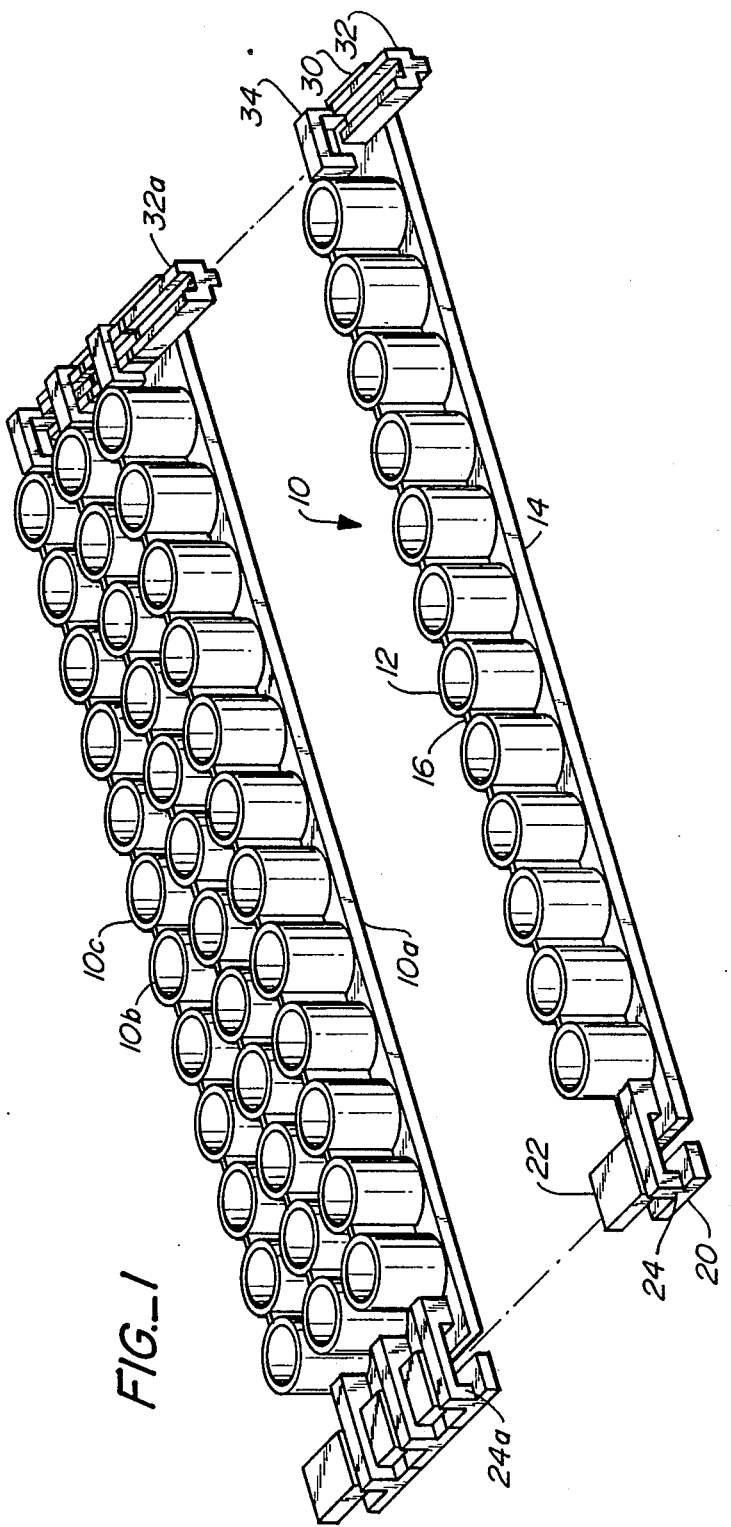

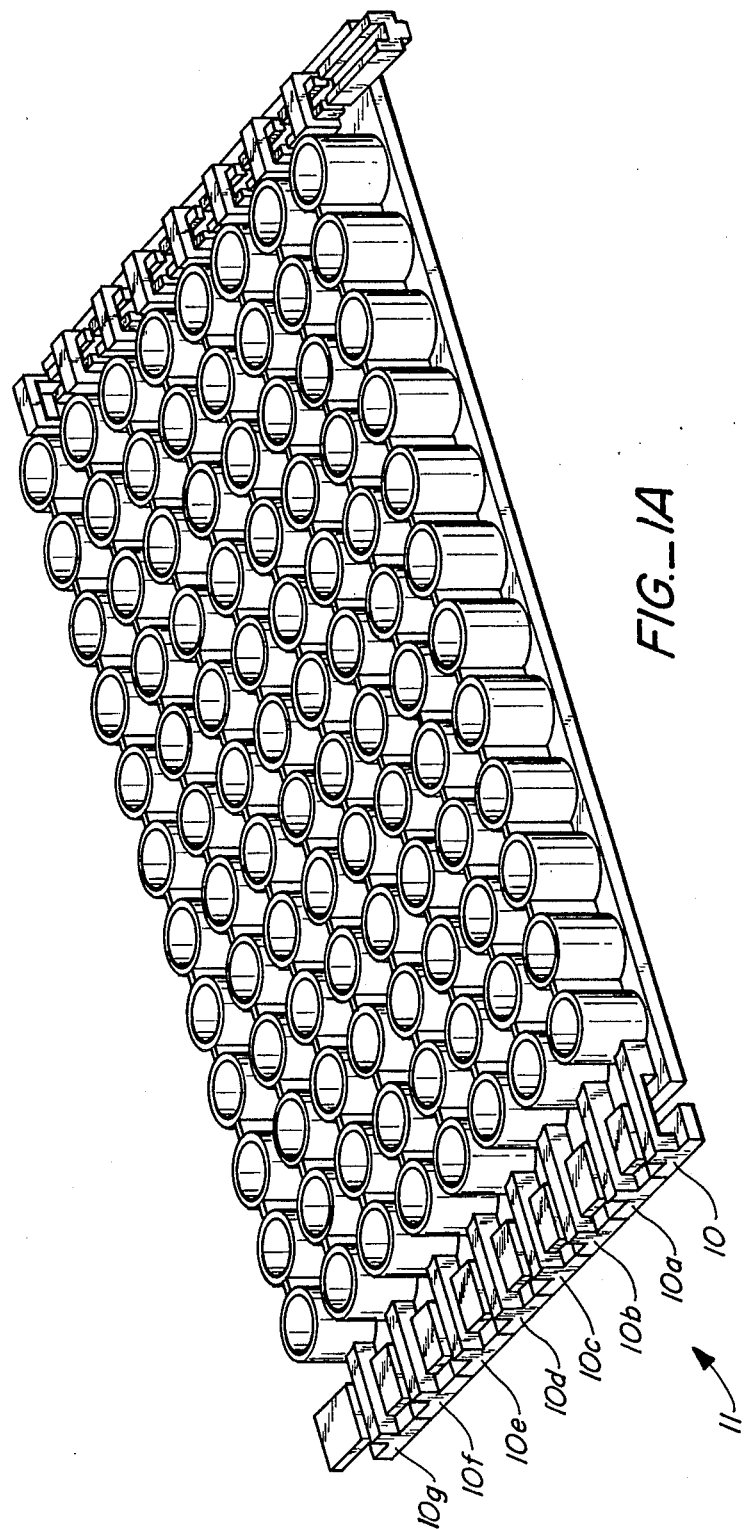
FIG._1A

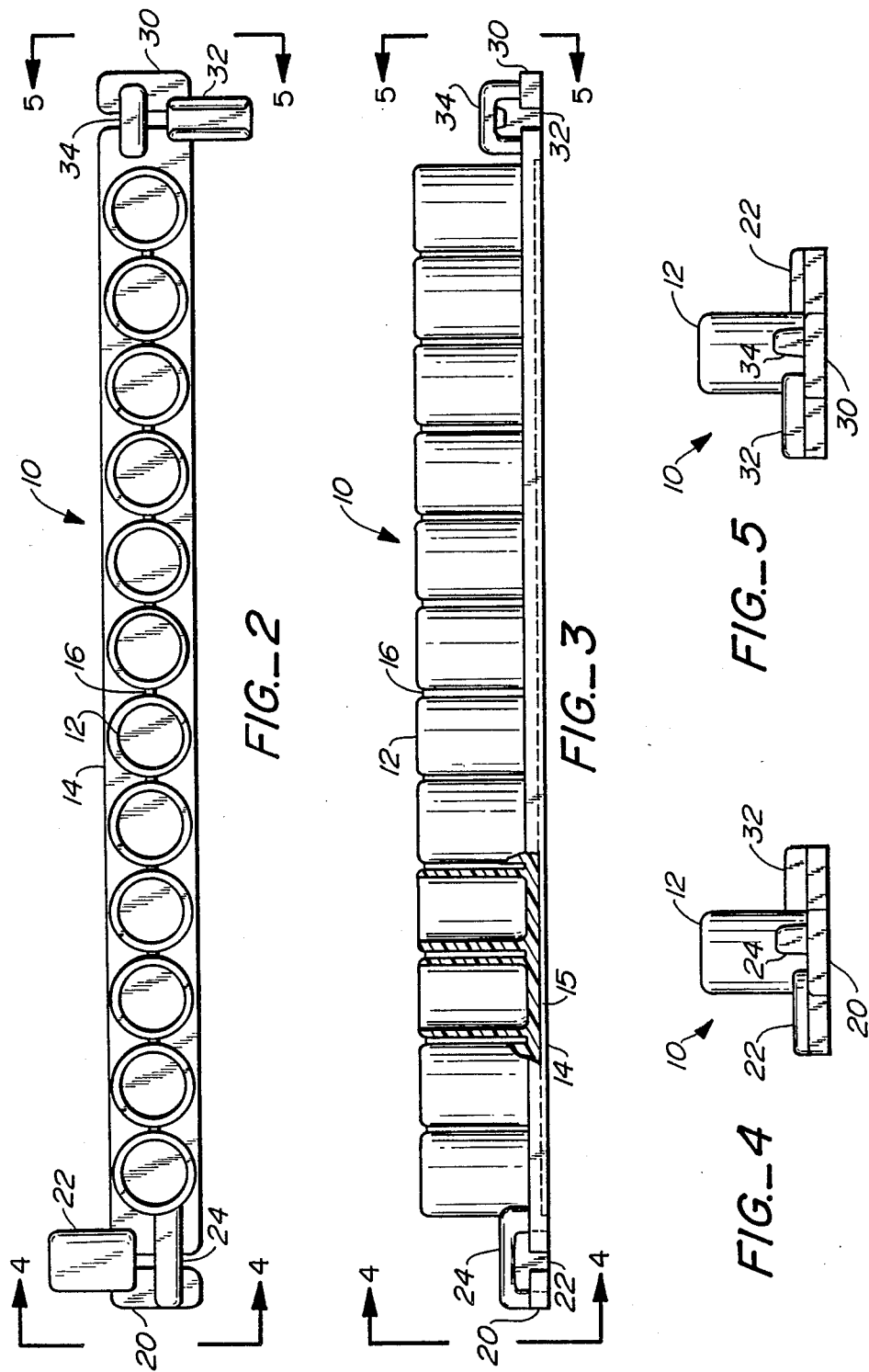

MULTIWELL ASSAY/CULTURE STRIP

BACKGROUND OF THE INVENTION

1. Field of the Invention

The present invention relates generally to laboratory equipment and apparatus, and more specifically to an improved multiwell assay and/or culture strip.

2. Description of the Prior Art

Multiwell trays are typically made of molded plastic, such as polystyrene, and have a number of generally identical well portions arranged in a row and column array. Each well in the tray is analogous to a small test tube. Multiwell trays are generally intended as single-use disposable items. A popular type of multiwell tray is the microplate (also known as microtiter plates, microtest plates, or simply, plates). A microplate is about the size of a postcard and about one-half inch thick, with ninety-six wells arranged in an array of eight rows by twelve columns. Microplates are widely used for growing (culturing) living cells and in performing a variety of research and diagnostic tests (assays) such as detection and identification of antibodies, viruses, bacteria, drugs or other substances. It is a common practice to treat or coat the wells of a microplate with biological substances such as antigens or antibodies for use in particular assays. Various steps routinely performed in the course of culturing cells or performing an assay can include inserting objects into the wells for mixing or sampling the contents, filling the wells with liquid, emptying the liquid from the wells, and photometric reading which consists of passing a beam of light through the well and its contents to be measured by a photosensitive detector.

As the use of microplates became more widespread, instruments were developed to perform and automate various steps of the culturing and assay procedure. An ad hoc standard configuration for microplate and well dimensions emerged as new manufacturers produced microplates or developed equipment intended to be compatible or competitive with those already in existence.

As many different types of assays were developed (and are still being developed), it became clear that, in many cases, the standard ninety-six-well microplate format represented an inconveniently large number of tests. To permit smaller numbers of tests to be performed conveniently, a number of manufacturers have produced modules or strips of wells corresponding to only one row or column of wells on a microplate. In keeping with the standard microplate configuration, these microwell strips generally contain either eight or twelve wells. All of the presently available microwell strips require the use of a rectangular retainer or frame member to hold the microwell strips. These frames have the same outside dimensions as the outer edge of a traditional microplate, and hold up to eight twelve-well strips or, alternatively, twelve eight-well strips. Therefore, a frame when completely filled with strips has the same dimensions and number of wells as a microplate.

The frame performs several functions. It holds the strips upright and facilitates handling since single strips usually tip over easily, spilling the well contents. The frame allows the user to assemble a microplate-sized unit with between one to eight rows or between one to twelve columns of wells. Since the frame itself matches the outer dimensions of a microplate, it allows the use of these microwell strips with certain microplate-compatible equipment. Each well in a strip is usually uniquely identified with a letter or number. Since the location of a particular well may be important in specific cultures or assays, each frame generally includes some visual or mechanical mechanism so that strips are uniformly aligned in the frame with their wells in the same sequence.

There are some inherent disadvantages associated with use of the frame. It is a component which is not directly involved in the culturing of cells or performance of the assay so its presence increases costs for production, packaging and handling. Use of a frame also increases the user's handling requirement since strips must be manually placed within the frame or removed from it to get the desired number of wells. Also, because the maximum capacity of any frame is ninety-six wells (eight twelve-well strips or twelve eight-well strips), multiple frames are required when more than ninety-six wells are desired. Also, although the strips are intended as single-use disposable items, the frame can represent a potential source of contamination if used more than once. This risk may predominantly occur in commercially available test kits or other packaging configurations where one frame is typically supplied with a full complement of strips.

SUMMARY OF THE INVENTION

The multiwell assay/culture strip of this invention provides an improved structure for a strip of wells as used for culturing cells and diagnostic testing. A preferred embodiment of the invention comprises a strip or segment of generally identical well portions (typically eight or twelve wells) in linear arrangement adjacent one another and supported by a common base, and terminating in a first end and a second end. The strip's first end bears a first tab or male linking member extending perpendicularly from the first end, and carries a first slot or female receiver member conditioned to accept and frictionally engage a first male linking member of a separate strip. The strip second end analogously bears a second tab or male linking member extending perpendicularly from the second end, but in the opposite direction from said first end male linking member, and carries a second slot or female receiver member conditioned to accept and frictionally engage a second male linking member of a separate strip. Thus, when a pair of separate strips are brought together into parallel alignment with one another so that the first nd male linking member of the initial strip is aligned with the first end female receiving member of the separate strip, and the second end male linking member of the initial strip is aligned with the second end female receiving member of the separate strip, the two strips may be connected by these respective, complementary connectors.

However, said first male linking member is specifically not engageable with a second female receiving member of a separate strip, nor is said second male linking member engageable with a first female receiving member of a separate strip. Thus, separate strips can only be assembled in one fashion (first end to first end, and second end to second end). In situations where the sequence of wells is important, wells on all linked strips will be similarly aligned. In addition, the visible differences between the first and second ends and their respective male and female members (e.g., width, height, shape) provide the user with a readily visible means of alignment. 15 Any number of separate strips may be linked together to assemble the desired size array of wells. For example, eight-well strips may be assembled to provide an array with sixteen, twenty-four, thirty-two, etc. wells, and twelve-well strips may be assembled to provide an array with twenty-four, thirty-six, forty-eight, etc. wells. Furthermore, when twelve eight-well strips, or eight twelve-well strips are assembled, the rectangle defined by the edges of the strips and the projecting linking members has the same "footprint" as a standard ninety-six-well micro plate, thus rendering the array suitable for standardized applications and microplate-compatible instruments, many of which use a carrier or holder where the microplate rests in a rectangular cut-out. Still further, any number of similar strips can be continuously assembled, rather than being limited to multiples of the frame's capacity.

A given strip's linking members engage a separate strip's complementary receiving members in a horizontal plane (parallel to the bases). This feature enables joinder and separation of separate strips upon a horizontal plane, such as a flat working surface, which minimizes the risk of splashing or spilling the contents of the wells if the strips must be joined or separated while the wells are filled with liquid.

The perpendicularly-extending first and second male linking members each include a lower surface which is coplanar with the strip base. Thus, these male linking members broaden the base of the strip beyond its normally linear contact with a working surface, and effectively prevent the strip from tipping over. This feature is important when the strip is used individually, without being assembled to a larger group of strips.

Thus, the present invention eliminates the need for a frame while maintaining all the advantages provided by the frame. The microplate configuration of present invention was developed to provide the following functions equivalent to presently available microplate strips and frames: stability against tipping for single strips; uniform alignment of wells in interlocked strips; and compatibility with "standard" microplate dimensions when eight twelve-well strips or twelve eight-well strips (ninety-six wells) are assembled.

The strip and tab design in the present invention also provides additional benefits not found in present strips and frames: the space required is defined by the desired number of strips rather than the frame; single strips which are filled with liquid can be handled, assembled and removed with minimal risk of spillage due to tipping or vertical engagement or removal in a frame; and any number of similar strips can be continuously assembled rather than being limited to multiples of the frame's capacity.

Other advantages associated with the elimination of a frame for multiwell strips are (a) reduction of production, packaging and handling costs both to the manufacturer and to the user, (b) increased speed and convenience in handling and (c) no risk of contamination from reusing a frame. The present invention permits single or multiple strips with filled wells to be removed and set aside for quality control or other testing (filled single strips which require frames can easily tip and spill when not in their frames). The tabs on the present invention in combination with the ends of the strip give the same rectangular "footprint" as a standard microplate so that when assembled, eight twelve-well strips or twelve eight-well strips can be used with most existing microplate-compatible equipment. However, the ability to continuously link large numbers of the present invention offers compatibility with faster, simpler and less expensive equipment than is presently required for handling strips in frames or for handling individual microplates.

BRIEF DESCRIPTION OF THE DRAWINGS

FIG. 1 is a perspective view of a series of multiwell assay/culture strips of this invention, illustrating an independent strip as aligned for engagement with a group of previously engaged strips;

FIG. 1A is a perspective view of a series of multiwell assay/culture strips of this invention, as assembled into a ninety-six well microplate;

FIG. 2 is a top plan view of a single multiwell assay/culture strip of this invention;

FIG. 3 is a partially cutaway side view of a single multiwell assay/culture strip of this invention;

FIG. 4 is a left end elevation view of a single multiwell assay/culture strip of this invention, illustrating a first end male linking member and female receiving member; and FIG. 5 is a right end elevation view of a single multiwell assay/culture strip of this invention, illustrating a second end male linking member and female receiving member.

DETAILED DESCRIPTION OF A PREFERRED EMBODIMENT

FIG. 1 is a perspective view of a series of multiwell assay/culture strips of this invention, illustrating an independent strip as aligned for engagement with a group of previously engaged strips. Strip 10 comprises a plurality (here twelve) of wells 12 in linear, side-by-side arrangement upon a base 14. Bridge portions 16 may connect the respective wells to provide added rigidity and strength. Strip 10 includes a first end portion 20, bearing a tab or male linking member 22 extending perpendicularly therefrom, and carrying a slot or female receiving member 24. Male linking member 22 is conditioned to engage a complementary female receiving member 24a on a separate, adjacent strip 10a. Strip 10a, as illustrated, is joined with adjacent strips 10b, 10c in like fashion.

Strip 10 also includes a second end portion 30, bearing a tab or male linking member 32 extending perpendicularly therefrom and carrying a slot or female receiving member 24. Tab 32 extends in the opposite direction from tab 22. As before, male linking member 32 is conditioned to engage a complementary female receiving member 34a on a separate adjacent strip 10a. However, male linking member 32 is specifically not engageable within female receiving member 24a, by virtue of its non-complementary geometry (e.g., it is too tall to fit within the opening of receiver member 24a). Similarly, male linking member 22 is specifically not engageable within female receiver member 34 (e.g., it is too wide to fit within the opening of receiver member 34). This link-specific aspect prevents misalignment of the respective strips 10, 10a, 10b, 10c.

FIG. 1A is a perspective view of eight twelve-well strips 10, 10a, 10b, 10c, etc., as assembled into a ninety-six well microplate 11. This combination yields the same rectangular "footprint" as a standard, unitary microplate, so that it can be used with most existing microplate-compatible equipment.

FIG. 2 is a top plan view of a single multiwell assay/culture strip of this invention. This view further illustrates the visible dimorphism of the strip's first and second ends. Of course, the respective first and second end's linking and receiving members could be of any practical shape or size, so long as they achieve the desired link-specific characteristics.

FIG. 3 is a partially cutaway side view of a single multiwell assay/culture strip of this invention. This view illustrates the relatively flat bottom surfaces of first end male linking member 22 and second end male linking member 32. It is these flat bottom surfaces, extending perpendicularly in opposite directions some short distance from base 14, that extend the footprint of an individual strip's base and provide it with additional stability.

This view also illustrates several desirable features of the wells and base of the inventive strip. First, the wells are designed with flat bottoms which are level, uniform in thickness and coplanar with one another to provide uniformity for photometric reading of results in which a filtered light-beam passes vertically through the well to measure optical density of the contents. The corners of the wells are slightly radiused to permit easier flushing of the well's contents and reduce residual drops of liquid which tend to form more easily in right angle corners. The depth and center-to-center spacing of the wells are similar to that of a standard microplate, achieving compatibility with existing reading, washing, sampling, and dispensing equipment. Furthermore, with reference to the base 14, the interior of the base includes a recessed portion 15 extending the length of the strip immediately beneath the aligned wells. This recessed area avoids contact with the working surface, and thus avoids scratches which could interfere with the photometric reading of the wells. In addition, the contour of this recessed area provides additional rigidity and strength to the overall strip.

FIG. 4 is a left end elevation view of a single multiwell assay/culture strip of this invention, illustrating a first end male linking member and female receiving member, while FIG. 5 is a right end elevation view illustrating a second end male linking member and female receiving member. These views further illustrate the dimosphism of the respective first and second ends, as well as the stabilizing base provided by the first and second male linking members 22, 32, respectively.

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims.

What is claimed as invention is:

1. A multiwell assay/culture strip comprising:
   a strip member having a base portion and a first and second end;
   a plurality of well portions supported on said base portion in linear, side-by-side arrangement;
   first male linking means located on said first end and extending some distance therefrom;
   first female receiver means located on said first end, said first female receiving means conditioned for releasable engagement with an identical first male linking means of another strip member;
   second male linking means located on said second end and extending some distance therefrom; and
   second female receiver means located on said second end, said second female receiving means conditioned for releasable engagement with an identical second male linking means of another strip member;
   wherein said first male linking means are not engageable with said second female receiving means, and said second male linking means are not engageable with said first female receiving means.

2. The multiwell strip of claim 1 wherein said first male linking means extends perpendicularly in a first direction from said first end, and said second male linking means extends perpendicularly in a second direction, opposite said first direction, from said second end.

3. The multiwell strip of claim 2 wherein said first and second male linking means each bears a bottom surface, said bottom surfaces being coplanar with said strip base.

4. The multiwell strip of claim 3 wherein said base includes a recessed portion beneath said well portions.

* * * * *